(12) United States Patent
Nolan et al.

(10) Patent No.: US 9,033,906 B2
(45) Date of Patent: May 19, 2015

(54) THERAPEUTIC COMPRESSION APPARATUS

(75) Inventors: Timothy J. Nolan, South Salem, NY (US); Guy Osborne, Trumbull, CT (US); Sundaram Ravikumar, Briar Cliff Manor, NY (US); Vikram Ravikumar, Briar Cliff Manor, NY (US)

(73) Assignee: Sun Scientific, Inc., Dobbs Ferry, NY (US)

( * ) Notice: Subject to any disclaimer, the term of this patent is extended or adjusted under 35 U.S.C. 154(b) by 0 days.

(21) Appl. No.: 12/855,185

(22) Filed: Aug. 12, 2010

(65) Prior Publication Data
US 2012/0041351 A1 Feb. 16, 2012

(51) Int. Cl.
- *A61F 5/00* (2006.01)
- *A61F 13/00* (2006.01)
- *A61F 15/00* (2006.01)
- *A61F 13/06* (2006.01)
- *A61F 13/08* (2006.01)

(52) U.S. Cl.
CPC .................................... *A61F 13/085* (2013.01)

(58) Field of Classification Search
USPC ......... 602/13, 23, 5, 60, 61, 62, 63, 75, 1, 53; 128/DIG. 20; 601/150, 148, 149, 151, 601/152; 606/201, 202
See application file for complete search history.

(56) References Cited

U.S. PATENT DOCUMENTS

| | | |
|---|---|---|
| 3,877,426 A * | 4/1975 | Nirschl ............................ 602/62 |
| 3,939,829 A | 2/1976 | Spann |
| 3,946,451 A | 3/1976 | Spann |
| 4,013,069 A | 3/1977 | Hasty |
| 4,030,488 A | 6/1977 | Hasty |
| 4,054,129 A * | 10/1977 | Byars et al. .................... 601/152 |
| 4,071,031 A | 1/1978 | Lowman |
| 4,186,738 A | 2/1980 | Schleicher et al. |
| 4,197,845 A | 4/1980 | Browning |
| 4,266,298 A | 5/1981 | Graziano |
| 4,320,746 A | 3/1982 | Arkans et al. |
| 4,399,815 A | 8/1983 | Bachorik |
| 4,402,312 A | 9/1983 | Villari et al. |
| 4,409,975 A | 10/1983 | Simhoni |
| D274,264 S | 6/1984 | Andersson |
| 4,730,610 A | 3/1988 | Graebe |
| 4,944,060 A | 7/1990 | Peery et al. |

(Continued)

OTHER PUBLICATIONS

International Search Report and Written Opinion for PCT/US2011/047539, issued Mar. 15, 2012.

*Primary Examiner* — Victoria J Hicks
(74) *Attorney, Agent, or Firm* — Nugent + Smith, LLP; Theresa O'Rourke Nugent

(57) ABSTRACT

A therapeutic compression apparatus having a primary wrap, a foot wrap and a stirrup is provided. The primary wrap encircles a first portion of a leg and applies compression thereto. The foot wrap encircles at least a portion of the foot and applies compression thereto. The foot wrap may be integrated with the stirrup, detachably connected or provided separately. The compression apparatus may be configured such that one or more bladders are provided therein. The compression apparatus may include a pressure gauge and pump for controlling an amount of pressure applied to the treatment site. A bladder assembly with a number of fluid bladder configurations is also provided for use within a compression apparatus. The bladder may be configured to provide a gradient pressure profile to the treatment site when filled.

11 Claims, 6 Drawing Sheets

(56) References Cited

U.S. PATENT DOCUMENTS

| | | |
|---|---|---|
| 4,977,891 A | 12/1990 | Grim |
| 5,085,214 A | 2/1992 | Barrett |
| 5,226,245 A | 7/1993 | Lamont |
| 5,328,445 A | 7/1994 | Spahn et al. |
| 5,412,822 A | 5/1995 | Kelly |
| 5,431,624 A | 7/1995 | Saxton et al. |
| 5,435,009 A | 7/1995 | Schild et al. |
| 5,449,339 A | 9/1995 | Drennan |
| 5,476,105 A | 12/1995 | Toth |
| 5,489,259 A | 2/1996 | Jacobs et al. |
| 5,666,681 A | 9/1997 | Meyer et al. |
| 5,711,760 A | 1/1998 | Ibrahim et al. |
| 5,765,564 A | 6/1998 | Ewing |
| 5,839,139 A | 11/1998 | Fink |
| 5,876,364 A | 3/1999 | Herbst |
| 5,913,841 A | 6/1999 | Lamont |
| 5,957,872 A | 9/1999 | Flick |
| 5,957,874 A | 9/1999 | Klein |
| 5,997,491 A | 12/1999 | Harris |
| 6,001,119 A | 12/1999 | Hampson et al. |
| 6,007,559 A * | 12/1999 | Arkans .................. 606/201 |
| 6,149,613 A | 11/2000 | Klein |
| 6,151,739 A | 11/2000 | Meyer et al. |
| 6,175,979 B1 | 1/2001 | Jackson |
| 6,260,221 B1 | 7/2001 | Grabell et al. |
| 6,290,662 B1 | 9/2001 | Morris et al. |
| 6,298,484 B1 * | 10/2001 | Beckman ........................ 2/22 |
| 6,351,863 B1 | 3/2002 | Meyer et al. |
| 6,358,219 B1 * | 3/2002 | Arkans .................. 601/152 |
| 6,494,852 B1 | 12/2002 | Barak et al. |
| 6,572,573 B1 | 6/2003 | Klein |
| 6,589,194 B1 | 7/2003 | Calderon et al. |
| 6,634,045 B1 | 10/2003 | DuDonis et al. |
| 6,689,079 B2 | 2/2004 | Flick et al. |
| 6,786,879 B1 | 9/2004 | Bolam et al. |
| 6,789,284 B2 | 9/2004 | Kemp |
| 6,877,178 B2 | 4/2005 | Chapman et al. |
| 6,968,585 B2 | 11/2005 | Shaw |
| 7,141,032 B2 | 11/2006 | Flam et al. |
| 7,258,676 B2 | 8/2007 | Calderon et al. |
| 7,276,037 B2 | 10/2007 | Ravikumar |
| 7,354,411 B2 | 4/2008 | Perry et al. |
| 7,850,629 B2 | 12/2010 | Ravikumar |
| 7,909,787 B2 | 3/2011 | Ravikumar |
| 7,967,766 B2 | 6/2011 | Ravikumar |
| 2001/0016960 A1 | 8/2001 | Grabell et al. |
| 2005/0070828 A1 | 3/2005 | Hampson et al. |
| 2005/0107728 A1 | 5/2005 | Vetters et al. |
| 2005/0187501 A1 | 8/2005 | Ravikumar |
| 2005/0187503 A1 | 8/2005 | Tordella et al. |
| 2005/0192524 A1 * | 9/2005 | Lipshaw et al. .............. 602/62 |
| 2007/0161933 A1 | 7/2007 | Ravikumar |
| 2007/0232973 A1 * | 10/2007 | Serola .................. 602/19 |
| 2008/0249441 A1 | 10/2008 | Avitable et al. |
| 2009/0260639 A1 | 10/2009 | Hsu et al. |
| 2009/0326576 A1 | 12/2009 | Ben-Hun |
| 2010/0087765 A1 | 4/2010 | Gainey |
| 2010/0100017 A1 | 4/2010 | Maguina |

* cited by examiner

 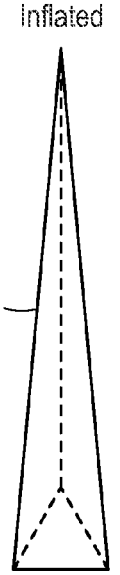  
FIG. 7        FIG. 8
 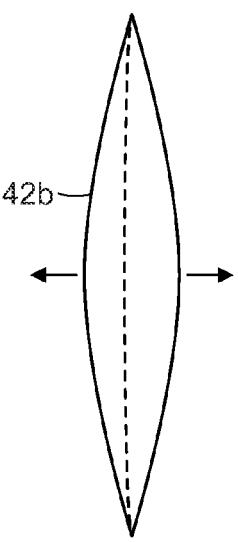  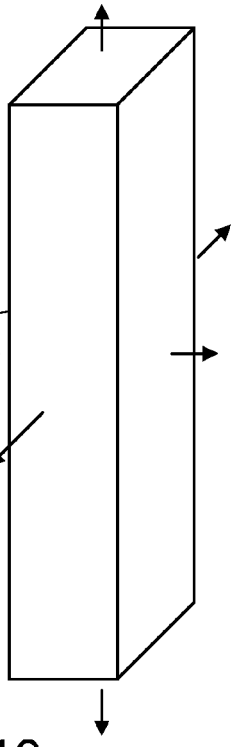
FIG. 9        FIG. 10

THERAPEUTIC COMPRESSION APPARATUS

BACKGROUND OF THE INVENTION

I. Field of the Invention

The subject invention is directed generally to a device for applying compression to a limb, and more particularly, to a therapeutic apparatus for applying compression to the leg of an individual in conjunction with the treatment of conditions such as chronic venous insufficiency and lymphedema. The apparatus includes a primary wrap, a foot wrap and a stirrup for applying compression to the lower leg and foot of a patient.

II. Background of the Related Art

Normally, a healthy leg muscle, for example, squeezes the deep veins of the legs and feet to help move blood back to the heart. One-way valves in the deep leg veins keep blood flowing back towards the heart. However, prolonged periods of standing or sitting can cause the walls of the deep leg veins to stretch. Over time, in susceptible individuals, this can weaken the vein walls and damage the valves, causing blood to pool in the veins and increase venous blood pressure. This may result in a condition known as chronic venous insufficiency (CVI).

Treatment of CVI typically involves the use of compression stockings or medical hosiery to decrease chronic swelling. Compression stockings are elastic stockings that squeeze the veins to improve venous circulation and prevent excess blood from flowing backward. Compression stockings can also help to heal skin sores or stasis ulcers that often present in conjunction with CVI. It is also common to employ compression bandages to apply pressure to the leg. In this regard, a bandage is applied with constant tension so as to produce graduated compression with the highest pressure at the ankle. However, the technique is difficult and is often done by highly skilled caregivers.

Highly effective mechanical compression devices have also been developed for treating CVI, which are disclosed, for example, in U.S. Pat. Nos. 7,276,037 and 7,559,908, the disclosures of which are incorporated by reference herein in their entireties. These devices include a flexible wrap that carries a manually inflatable air bladder and is adapted to be securely positioned around the leg of an individual to apply localized pressure to a treatment site. The device also includes a fluid-filled wound dressing that can be applied directly to the skin for applying localized pressure and even a medicament to a venous ulcer when it is enveloped by the flexible wrap. While this device is effective for applying localized compression to the leg, it is not configured to apply localized compression to the foot to prevent swelling and further improve venous circulation.

Lymphedema, also known as lymphatic obstruction, is another condition of localized fluid retention and tissue swelling, and is caused by a compromised lymphatic system. Treatment for lymphedema varies depending on the severity of the edema and the degree of fibrosis of the affected limb. The most common treatments for lymphedema are manual compression lymphatic massage, compression garments or bandaging. Elastic compression garments are typically worn by persons with lymphedema on the affected limb following complete decongestive therapy to maintain edema reduction.

Compression bandaging, also called wrapping, involves the application of several layers of padding and short-stretch bandages to the involved areas. Short-stretch bandages are preferred over long-stretch bandages (such as those normally used to treat sprains), as the long-stretch bandages cannot produce the proper therapeutic tension necessary to safely reduce lymphedema and may in fact end up producing a tourniquet effect. During activity, whether exercise or daily activities, the short-stretch bandages enhance the pumping action of the lymph vessels by providing increased resistance for them to push against. This encourages lymphatic flow and helps to soften fluid-swollen areas.

Known methods for CVI and lymphedema treatment, like compression bandaging, have several disadvantages. The bandaging is time consuming and the effectiveness is limited to the skill of the provider. In some instances, bandages can be applied too tightly or too loosely and may slip from their intended position, decreasing their effectiveness. When this occurs, bandages must be taken off and reapplied, further increasing the time of application and decreasing the consistency of application of the therapy.

The effectiveness of many of the current compression therapies is limited by the application of current products. Because current compression therapy is done either with manual wraps or electromechanical systems, they require either a skilled medical processional to apply and/or the need for the patient to be stationary for extended periods of time. Although stockings and/or bandages can be worn by patients and self-administered, they are very difficult for the patient to put on and pose a challenge for unskilled medical professionals to apply consistently and effectively.

The apparatuses, methods and systems of the subject invention provide benefits and advantages that may overcome a number of problems with respect to known compression technologies, particularly the problems that arise due to the difficulty of applying current compression wrap technologies. The subject invention provides an alternative to known technologies that employ tight-fitting therapeutic elastic garments, which cause patients discomfort, and lose their elasticity and therefore their effectiveness over time. Those skilled in the art will readily appreciate that it would be beneficial to provide a therapeutic compression device for treating CVI and lymphedema that is adapted and configured to apply localized compression to the leg and foot to prevent swelling and further improve venous circulation, that may also be self-administered by a patient effectively.

SUMMARY OF THE INVENTION

The subject invention is directed to a therapeutic compression apparatus. The therapeutic compression apparatus comprises: a primary wrap, a foot wrap and a stirrup. The primary wrap encircles at least a first portion of a leg and applies compression thereto. The primary wrap has a horizontal proximal edge for positioning towards a knee of the leg, a horizontal distal edge for positioning towards an ankle of the leg, and first and second peripheral edges perpendicular to the horizontal proximal edge and the horizontal distal edge. The foot wrap encircles at least a portion of a foot of the leg to apply compression thereto. The stirrup is integrated with the primary wrap along the horizontal distal edges for securing the primary wrap to the leg, the stirrup being positioned between the primary wrap and the foot wrap.

The therapeutic compression apparatus may further comprise at least one bladder operatively associated with the primary wrap for applying pressure to a treatment site on the leg. The primary wrap may include at least one interior pocket for accommodating the at least one bladder. Alternatively, the at least one bladder may be integral with the primary wrap. One or more means for attaching the primary wrap may be operatively associated along the first and second peripheral edges of the primary wrap for securing the primary wrap around the leg.

The at least one bladder may be adapted and configured to form a predetermined gradient pressure profile when the at least one bladder is filled. The at least one bladder may be one of a wedge-shaped bladder, a cone-shaped bladder, a disk-shaped bladder or a rectangular-shaped bladder. The at least one bladder may also include a plurality of fluid chambers. The therapeutic compression apparatus may further comprise at least one means for adjusting pressure coupled to the at least one bladder for controlling an amount of pressure supplied to the treatment site by the primary wrap.

The foot wrap may be attached to the stirrup. The foot wrap may be configured to envelope toes of the foot and/or configured to envelope a heel of the foot. The foot wrap may also be configured as an adjustable strap around the foot.

The therapeutic compression apparatus may further comprises an adjustable belt along a proximal horizontal edge of the primary wrap for securing the primary wrap around the leg. The primary wrap may be formed at least in part of a non-elastic composite material comprising a plurality of distinct layers. In one embodiment, the composite material may comprises three distinct layers: an inner laminate layer, an outer hook-compatible layer, and a middle non-elastic layer provided between the inner and outer layers. The composite material may also be provided with a plurality of stitched darts and gathers for contouring the primary wrap to the leg.

The subject invention is also directed to a bladder assembly for a compression apparatus for providing pressure to a limb. The bladder assembly comprises: at least one bladder having first and second flexible walls secured to one another about a peripheral edge thereof to form an air pocket; and at least one spot weld provided in a predetermined location inward of the peripheral edge connecting the first and second walls to one another to define a plurality of chambers within the bladder. The geometric placement of the at least one spot weld determines a pressure profile of the at least one bladder.

An inflation device for inflating the air pocket through at least one inflation port may be provided in the first wall of the bladder assembly. The inflation device may be detachable from the at least one inflation port. At least one pressure valve may be operatively associated with the inflation device for controlling an amount of pressure within the air pocket.

These and other aspects of the contacts of the subject invention will become more readily apparent from the following description taken in conjunction with the drawings.

BRIEF DESCRIPTION OF THE DRAWINGS

So that those having ordinary skill in the art to which the subject invention pertains will more readily understand how to make and use the apparatuses of the subject invention, preferred embodiments thereof will be described in detail herein below with reference to the drawings, wherein:

FIG. 7 is a cross-sectional view of a wedge-shaped bladder in a non-inflated state (left) and an inflated state (right);

FIG. 8 is a cross-sectional view of a cone-shaped bladder in a non-inflated state (left) and an inflated state (right);

FIG. 9 is a cross-sectional view of a disk-shaped bladder in a non-inflated state (left) and an inflated state (right); and FIG. 10 is a cross-sectional view of a rectangular-shaped bladder in a non-inflated state (left) and an inflated state (right).

DETAILED DESCRIPTION OF THE PREFERRED EMBODIMENTS

Figure 1:
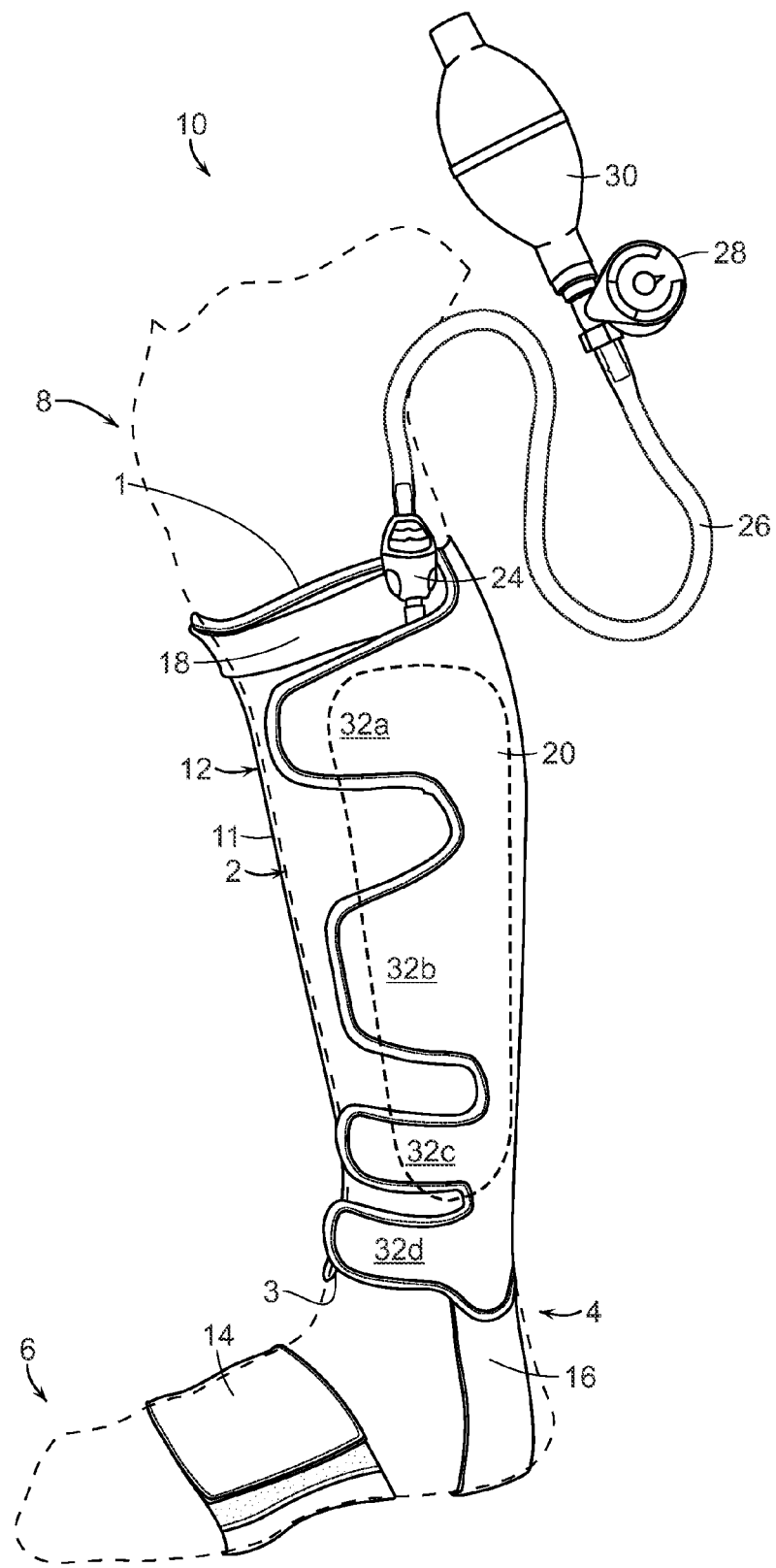
FIG. 1 is a perspective view of a compression apparatus according to the subject invention wrapped around a right leg and foot of a user having both a stirrup at a base of the foot and an adjustable strap below the knee, the apparatus having a pocket provided on an internal surface of the primary wrap (shown with hidden lines) for securing a fluid bladder, the bladder being provided with a detachable air pump and pressure gauge, and the primary and foot wraps being detached from each other.

Preferred embodiments of the subject invention are described below with reference to the accompanying drawings, in which like reference numerals represent the same or similar elements. One of ordinary skill in the art would appreciate that while the apparatuses discussed herein relate to compression therapy of the leg and foot, the scope of the invention is not limited to those exemplary applications and may be sized and shaped for the anatomical portion for which compression therapy is needed.

The subject invention provides compression to the extremities, including for example, the lower leg and foot, in a manner that is simpler and more convenient than current systems. The subject invention provides system for providing compression and preventing swelling of the foot using a non-elastic binder and bladder which can be used for compression. The bladder is provided within a non-elastic wrap and creates compression in a manner that allows for consistent measuring of the pressure supplied, as well as safe, comfortable, convenient, effective, self-application by the patient.

Referring now to FIG. 1, there is illustrated an exemplary embodiment of a therapeutic compression apparatus 10 according to the subject invention in which the exterior surface 11 of the primary wrap 12 of the compression apparatus 10 is shown in a wrapped state around a patient's right leg. The compression apparatus 10 is adapted and configured to supply compression of a lower leg 2 and foot 6 of a patient. The compression apparatus 10 consists of a primary wrap 12 which encircles the lower leg 2 and may be utilized for applying compression to the lower leg 2. The primary wrap 12 has an associated bladder 22 provided on an inner surface 9 of the primary wrap 12. As shown in FIG. 1, the primary wrap 12 encircles the lower leg 2, and when the bladder 22 is filled or inflated, compression is applied to a desired treatment location. Notably, the primary wrap 12 is made of a non-elastic material which allows for increased localized compression of the treatment site. The compression apparatus 10 also includes either a permanent or detachable pressure gauge 28 which is capable of being detached at the inlet port 24. A pump 30 is provided for manually pumping air into the bladder 22 through the tube 26. Additional features of the primary wrap 12, foot wrap 14, and bladder 22 will be described in turn herein.

The primary wrap 12 may be attached to a patient's lower leg 2, for example, by encircling the wrap about the lower leg 2 and attaching it at the peripheral edges 5 and 7 with any number of connecting structures. Hook and loop fastening tabs, such as connecting tabs 32a, 32b, 32c, 32d illustrated in FIGS. 1, and 2A-2B can be used to connect the opposing peripheral edges 5 and 7 of the primary wrap 12 and secure it about the lower leg 2. Hook and loop fastening tabs, buckles, straps, snaps or other known structures for fastening the primary wrap 12 to itself may also be used to attach the primary wrap 12 around the patient's limb. The number and position of the connecting tabs 32a, 32b, 32c, 32d may be selected based on the anatomical location of the patient's therapeutic site so that the primary wrap 12 is secured comfortably without causing bunching or sagging of the primary wrap 12 material and causing discomfort to the patient.

Figure 3:
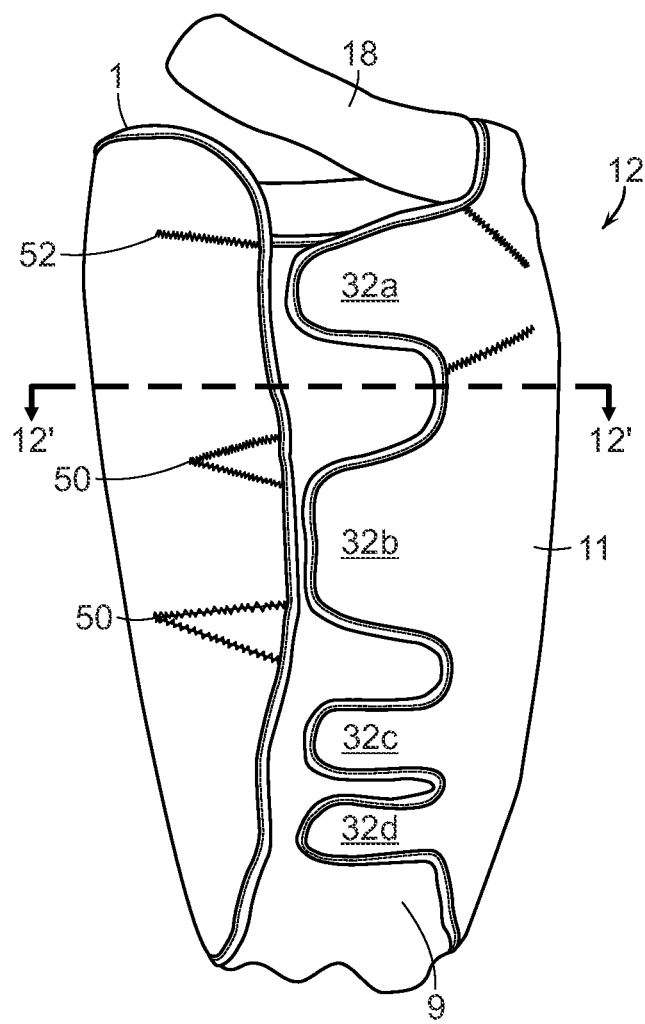
FIG. 3 is an elevational view of the exterior surface of the an upper section of the primary wrap according to the subject invention having a number of stitched darts and gathers for contouring around a leg, the primary wrap being illustrated to show a majority of the exterior surface of the primary wrap.

At a horizontal proximal end 1 of the primary wrap 12 towards the knee 8, an optional garter or adjustable belt 18 may be provided to further secure the primary wrap 12 about the lower leg 2. The adjustable belt 18 may be connected around the leg 2 using a connecting tab, buckle or other known connecting structures. As shown in FIG. 3, the primary wrap 12 is also manufactured with a number of stitched darts 50 and gathers 52 which are strategically placed to contour the primary wrap 12 around the specific limb being treated.

Figure 4:
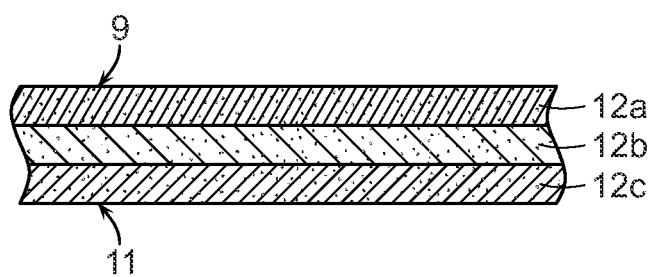
FIG. 4 is a cross-sectional view, taken along line 12'-12' of FIG. 3 illustrating the composite material of the primary wrap of the subject invention, which has three discrete layers.

The primary wrap 12 is preferably made of a composite material that is non-elastic and has one or more wicking layers. Because the material is non-elastic, the primary wrap 12 remains stiff and does not stretch when the bladder 22 is filled, or inflated, for example. Referring to FIG. 4, the composite material of the primary wrap 12 has three discrete layers 12a, 12b, and 12c as shown. The inner layer 12a is in contact with the patient's skin and includes an interior surface 9 that is non-elastic and is preferably made of a wicking, non-hook and loop compatible material. The wicking feature of this inner layer 12a pulls perspiration and other unwanted moisture away from the limb being treated. The non-hook and loop-compatible nature of the inner layer 12a is desirable so that the primary wrap 12 will not get caught on the connecting tabs 32a, 32b, 32c, 32d, if hook and loop fastening tabs, are used, for example. The non-hooking material against the patient's skin also reduces irritation, which may be caused from a hooking material. The outer layer 12c has at least a portion which is hook compatible in order for the connecting tabs 32a, 32b, 32c, 32d to be secured at the peripheral edge of the primary wrap 12 about the limb. The bottom surface of the outer layer 12c is the exterior surface 11 of the primary wrap 12 and is also non-elastic and breathable. The inner layer 12b, located between the inner and out layers 12a and 12c, is typically made of a breathable, laminate material.

Figure 2A:
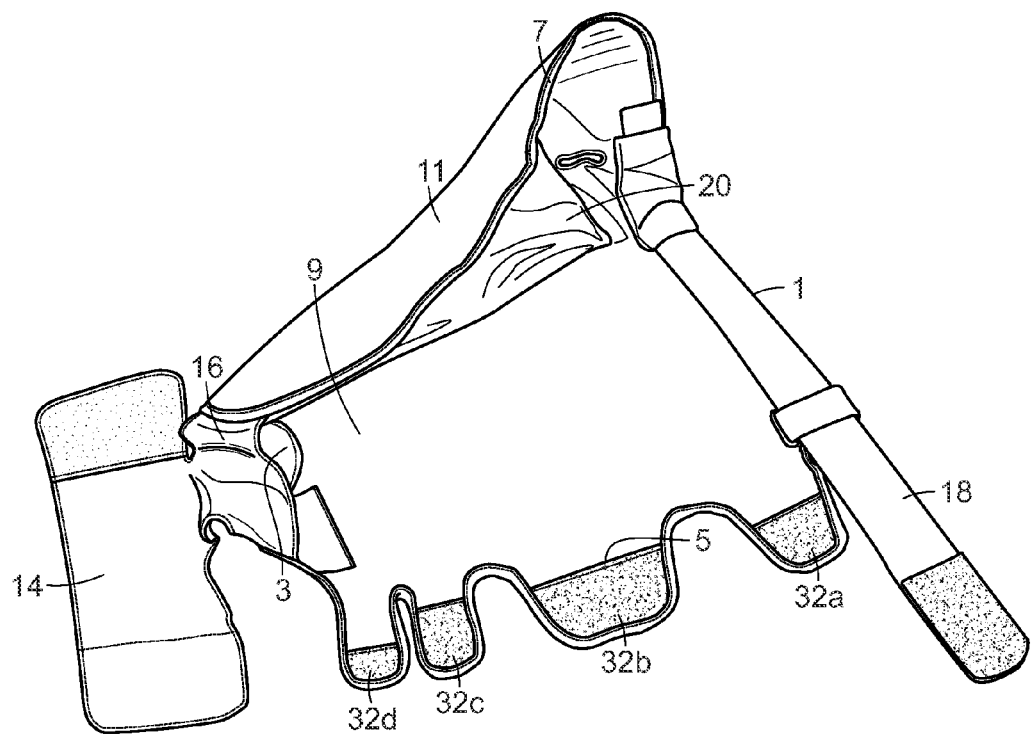
FIG. 2A is a perspective view of the compression apparatus of FIG. 1 in which the primary and foot wraps are illustrated in an unwrapped state, the interior surface of the wrap is shown, and the foot wrap is shown to be integrated with the stirrup.
Figure 2B:
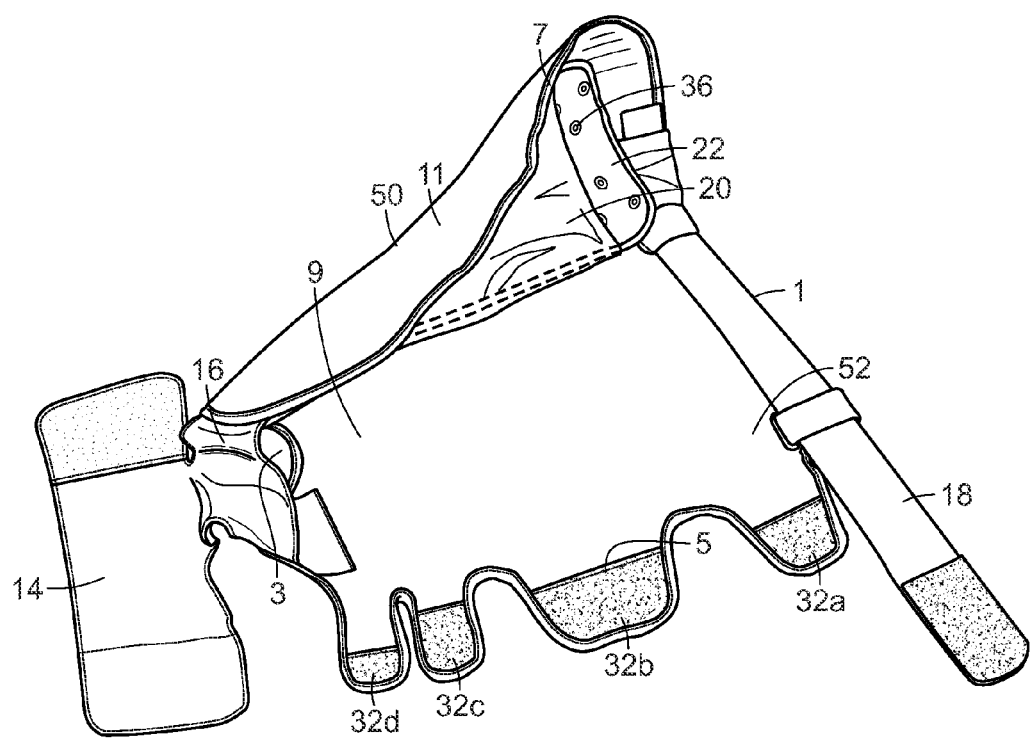
FIG. 2B is perspective view of the compression apparatus of FIG. 1 in which the primary wrap and the foot wrap, are illustrated in an unwrapped state, the interior surface of the primary wrap is shown having a bladder within a pocket of the primary wrap, and the foot wrap is shown to be integrated with the stirrup.

Referring to FIGS. 2A-2B, a stirrup 16 is also provided to help to secure the primary wrap 12 in place around the base of the foot 6. As best seen in FIG. 1, the stirrup 16 encircles a portion of the foot 2, and is connected to the horizontal distal edge 3 of the primary wrap 12 at two points on either side of the primary wrap 12 near the ankle 4. The stirrup 16 is located between the primary wrap 12 and the foot wrap 14. As shown in FIGS. 2A-2B, the stirrup 16 is typically one continuous piece of elastic material connected to and integrated with the foot wrap 14.

The foot wrap 14 of the compression apparatus 10 encircles the foot 6 and, like the primary wrap 12, may be similarly utilized for both applying compression to the foot 6 or alternatively as a protective garment for wound care dressings. The foot wrap 14 helps to prevent swelling of the foot 6. The swelling may occur on its own, or as a result of compression of the lower leg 2. The foot wrap 14 may be optionally made of a continuous piece of material with the stirrup 16, as shown in FIGS. 2A-2B. Alternatively, as shown in FIG. 1, the foot wrap 14 may be provided independently from the primary wrap 12.

The foot wrap 14 is typically formed of an elastic material, but may also be formed of a non-elastic material or a combination of the two. The foot wrap 14 may be a single piece of connected material. Alternatively, the foot wrap 14 may also be secured about the foot 6 by any number of mechanical securing devices such as one or more hook and loop fastening tabs as shown in FIG. 1, or by straps, buckles, snaps, and the like. In this embodiment, the foot wrap 14 provides compression to the foot 6 by pulling and tightening a hook and loop fastening tab, thereby applying pressure around the foot 6.

The foot wrap 14 may have a number of configurations depending on the therapeutic needs of the patient. The foot wrap 14 may be open-toed to expose the toes of the patient's foot 6 as shown in FIG. 1. Alternatively, the foot wrap 14 may be configured as a close-toed boot. In addition, the foot wrap 14 may have an open heel as shown in FIG. 1 or have a closed heel similar to a boot (not shown).

The primary wrap 12 supplies compression to a patient's limb by non-elastically holding at least one bladder 22 around the treatment site. In one embodiment, for example, localized pressure is provided by the compression apparatus 10 near the saphenous vein of the lower leg 2. As shown in FIG. 2B, the primary wrap 12 covers the bladder 22 associated with the primary wrap 12. The fluid within the bladder 22 may be a liquid, a gas or a gel. The bladder 22 serves to provide compression to the leg 2 when the bladder 22 is filled within the compression apparatus 10.

The bladder 22 may be inserted into one or more pockets 20 provided within the primary wrap 12 for storing the bladder 22 at a location where compression will be primarily applied. In this embodiment, the bladder 22 is detachable from the compression apparatus 10. In another embodiment, the bladder 22 is permanently integrated within the primary wrap 12 and not detachable (not shown).

According to the subject invention, the bladder 22 may have a number of additional features for monitoring, setting and adjusting the pressure required for a desired therapeutic regimen. In an exemplary embodiment illustrated in FIGS. 1 and 5, the bladder 22 includes a pressure gauge 28. The pressure gauge 28 is a pressure measuring instrument, such as a manometer, which measures the pressure differential between a closed pressure applied within the bladder 22 and an open pressure at the other of the pressure gauge 28. The increase in the measured pressure depends on the density of the liquid used and the diameter of the tubing.

Figure 5:
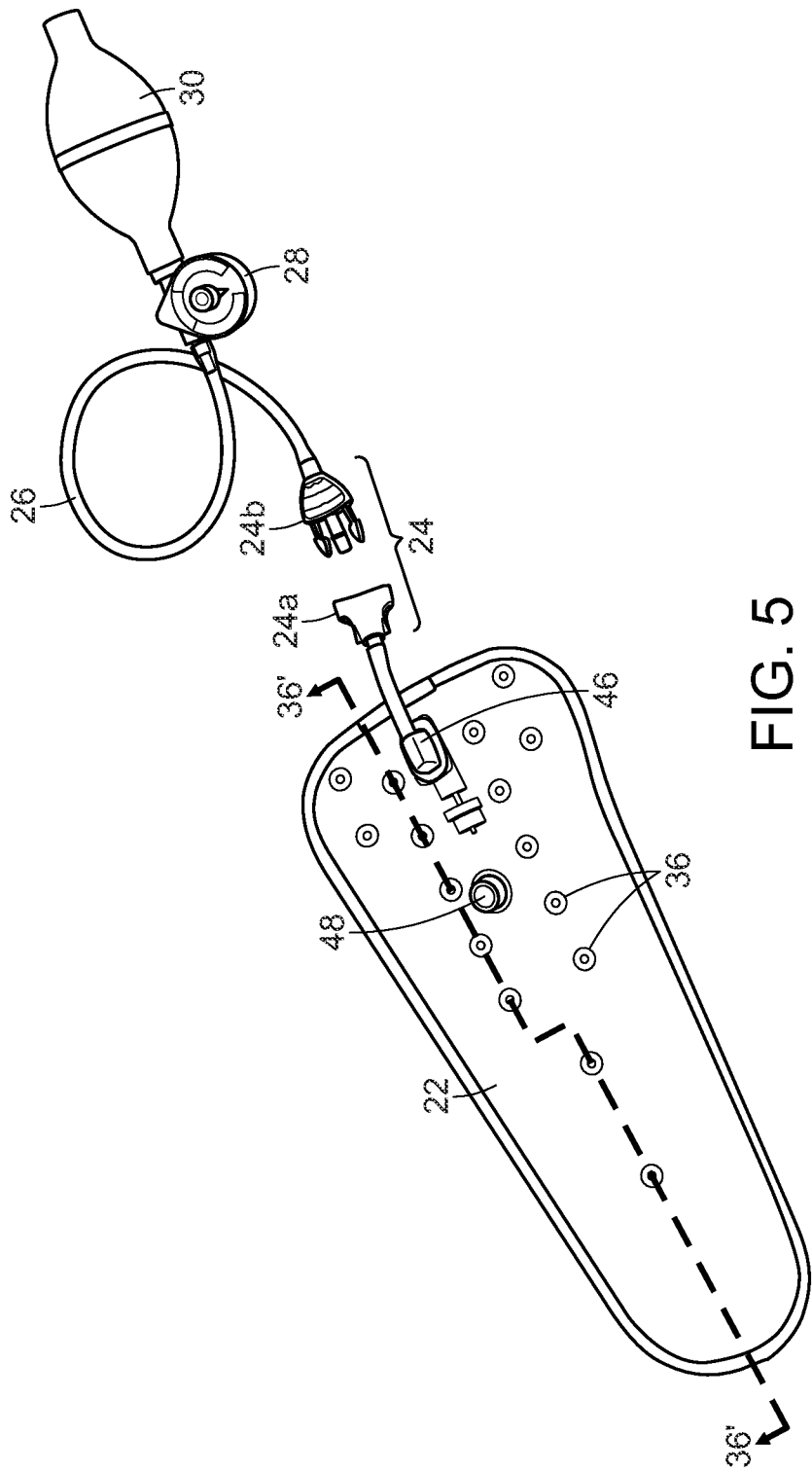
FIG. 5 is an exploded perspective view of a bladder having a plurality of spot welds, a pressure gauge and air pump are also illustrated as detached from the bladder according to the subject invention.

The pressure gauge 28 works in conjunction with the fluid or air pump 30 which pumps air into the bladder 22 through an inflation tube 26 at the inflation inlet 24a. The pump 30 may be a manual pump or an electronic pump for providing air to the bladder 22. An overflow valve 46 may also be provided and limits the amount of air capable of entering the bladder 22, along with a one-way valve 48 for releasing air from within the bladder 22, thereby lowering the pressure within the bladder 22. As shown in FIG. 5, the pressure gauge 28 and pump 30 may be detachably provided from the bladder 22 at a connector 24b.

In another embodiment, the bladder 22, itself, may serve as its own pressure gauge, in which the distention of the bladder 22 as it inflates indicates an amount of pressure within the bladder 22. In this instance, the pressure within the bladder 22 is pre-calibrated. Alternatively, more than one bladder 22 can be used, or a bladder 22 having multiple chambers can be used such that the distention of one or more of the bladders 22 or bladder chambers signifies the internal pressure. The subject invention provides pressure within the bladder 22 typically within the range of 20-50 mm Hg.

Figures 6A, 6B:
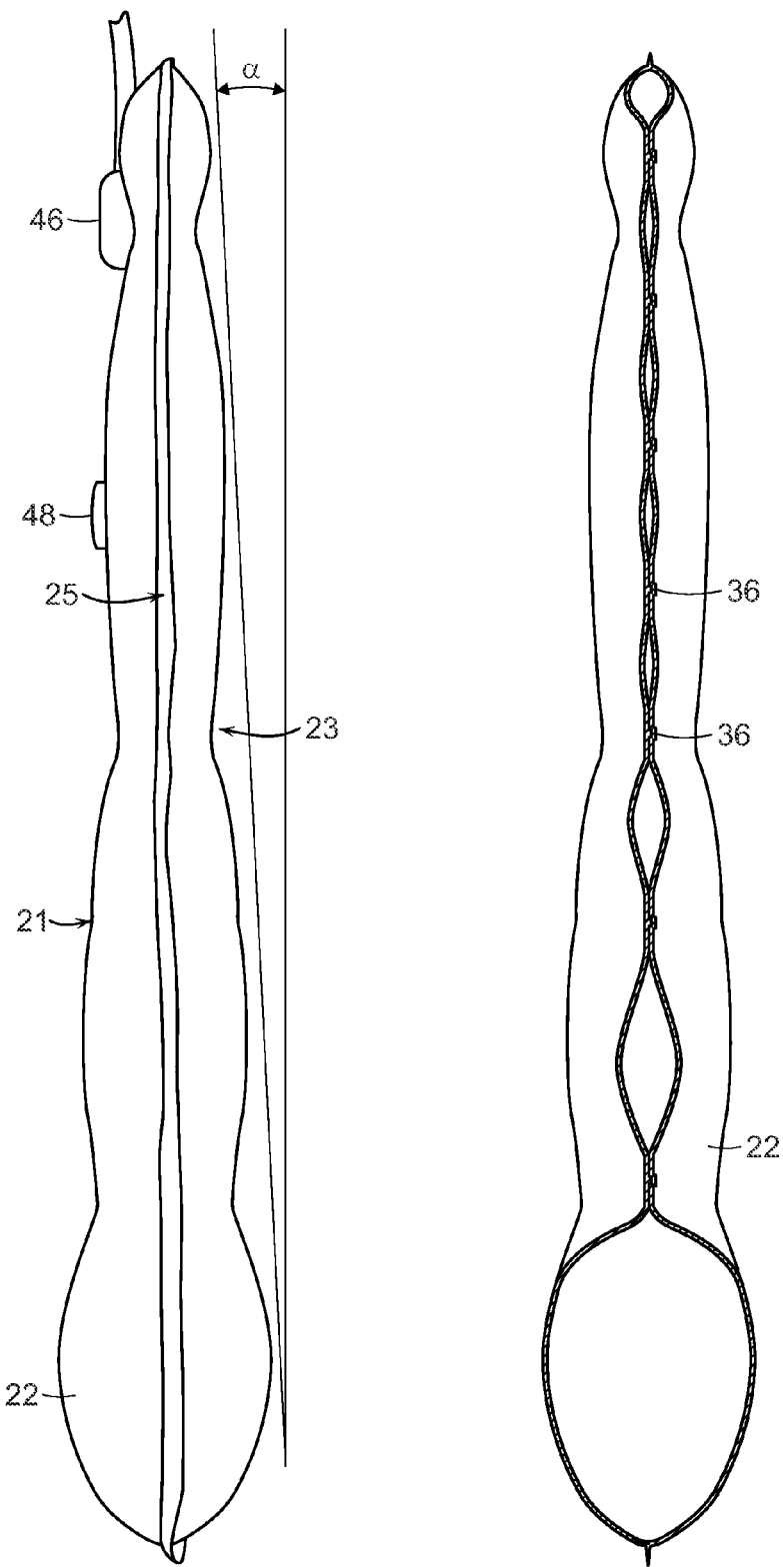
FIG. 6A is an elevational side view of the inflated bladder of FIG. 5 in an inflated condition.
FIG. 6B is a cross-sectional view taken along line 36'-36' illustrating how the strategically positioned spot welds in the bladder serve to join the upper and lower walls of the bladder to form a desired gradient profile.

A number of different embodiments of a bladder 22 can be used in the compression apparatus 10 of the subject invention. FIG. 5 shows a perspective view of one embodiment of a bladder 22 having a plurality of spot welds 36 according to the subject invention. The spot welds 36 are strategically placed within the bladder 22 in a predetermined pattern based on the desired gradient profile relative to the compression needed at the patient's treatment site. FIG. 6A is a side view of an inflated bladder 22 illustrated in FIG. 5 inflated to form an angle α relative to the horizontal axis of the bladder 22. The bladder 22 has a first side wall 21 and a second side wall 23 which are sealed together along a peripheral edge seam 25. Spot welds 36 are strategically positioned to join the first and second side walls 21 and 23 to one another. These spot welds 36 enable the bladder 22 to change the gradient profile and take on a number of configurations when inflated. The geometric placement of the spot welds 36 within the bladder 22 allows increased inflation of certain portions of the bladder 22, and can create one or more fluid chambers within the bladder 22. FIG. 6B is a cross-sectional view of an inflated bladder 22 taken along line 36'-36'. When the bladder 22 is used within a primary wrap 12, the bladder 22 inflates more at one end of the primary wrap 12 than the other, creating a gradient compression profile, as shown in FIG. 5. This configuration is particularly useful when compression is needed to improve fluid movement (blood, lymph, etc) within the body.

In addition to the bladder 22 having spot welds 36 illustrated in FIGS. 5 and 6B, several other bladder configurations shown in FIGS. 7-10 may be used within the compression apparatus 10 of the subject invention. FIG. 7 is a cross-sectional view of a wedge-shaped bladder in a non-inflated state 38a (left) and an inflated state 38b (right) which may be used in the compression apparatus 10 according to the subject invention. The wedge-shaped bladder 38b provides a comfortable and efficient gradient profile to the lower leg 2 when inflated and positioned within the primary wrap 12. The wedge-shaped bladder 38b has a pyramidal shape, as illustrated in FIG. 7 when inflated. One of the three pyramidal sides may be rigid, to prevent distention of the wedge-shaped bladder 38b in a direction away from the desired treatment area. Alternatively, the side closest to the treatment area may be attached or connected to a rigid material placed in a pocket 20 of the primary wrap 12 to prevent distention of the wedge-shaped bladder 38b in a direction away from the desired treatment area. The wedge-shaped bladder 38b is preferable to accommodate the normal anatomy where the ankle 4 is thinner than the lower leg 2. Thus, when the wedge-shaped bladder 38b is placed on the leg 2, the thinner portion is positioned towards the knee 8 and the thicker end is positioned towards the ankle 4. Referring now to FIG. 8, the cone-shaped bladder 40b, is similar to the wedge-shaped bladder 38b, and forms a cone when inflated. The inflated cone-shaped bladder 40b is preferable for use in normal anatomy in which the ankle 4 is thinner than the lower leg 2.

Turning to FIG. 9, a cross-sectional view of a disk-shaped bladder in a non-inflated state 42a (left) and an inflated state 42b (right) is shown. The disk-shaped bladder 42b is formed from two walls and has a disk or saucer shape when inflated. The rectangular-shaped bladder shown in a non-inflated state 44a (left) and an inflated state 44b (right) provides added benefits over the disk-shaped bladder 42b. The rectangular-shaped bladder 44b is also known as a three-dimensional bladder that allows for compression without bulging or distention in a direction away from the treatment area. The rectangular-shaped bladder 44b inflates uniformly throughout its length and width. This uniform inflation reduces the bulging that may occur at the center of the disk-shaped bladder 42b illustrated in FIG. 9. The walls of the rectangular-shaped bladder 44b can be elastic or inelastic. Alternatively, a combination of both inelastic and elastic walls may be used. One or more portions of the walls of the rectangular-shaped bladder 44b may be formed of a rigid material or attached to a rigid material placed within the pocket 20 of the primary wrap 12 in order to avoid distention.

While the subject invention of the present disclosure has been described with respect to preferred and exemplary embodiments, those skilled in the art will readily appreciate that various changes and/or modifications can be made to the invention without departing from the spirit or scope of the invention as described herein.

What is claimed is:

1. A therapeutic compression apparatus, comprising:
a) a primary wrap for encircling at least a first portion of a leg for applying compression thereto, the primary wrap having a horizontal proximal edge for positioning towards a knee of the leg, a horizontal distal edge for positioning towards an ankle of the leg, and first and second peripheral edges generally perpendicular to the horizontal proximal edge and the horizontal distal edge, wherein the primary wrap is made of a composite material comprising an inner layer having a non-elastic interior surface made from a wicking, non-hook and loop compatible material configured to pull moisture away from a treatment area, an outer hook-compatible layer having a non-elastic breathable bottom surface which forms an exterior surface of the primary wrap, and a middle laminate layer made of a breathable, laminate material disposed between the inner layer and the outer hook-compatible layer;
b) a foot wrap for encircling at least a portion of a foot of the leg to apply compression thereto;
c) a stirrup integrated with the primary wrap along the horizontal distal edge for securing the primary wrap to the leg, the stirrup being positioned between the primary wrap and the foot wrap; and
d) at least one inflatable bladder operatively associated with the primary wrap for applying pressure to a treatment site on the leg, wherein the at least one inflatable bladder is detachable from the compression apparatus and is wedge-shaped having three sides configured to define a pyramidal shape when inflated, with one of the three sides being rigid to prevent distension thereof in a direction away from a treatment area when operatively disposed in the primary wrap, and having a thinner portion configured to be positioned toward the knee and a thicker end configured to be positioned toward the ankle, wherein the composite material is non-elastic and configured to remain stiff and prevent stretching of the primary wrap during inflation of the at least one inflatable bladder.

2. A therapeutic compression apparatus as recited in claim 1, wherein the primary wrap defines at least one interior pocket for securing the at least one inflatable bladder.

3. A therapeutic compression apparatus as recited in claim 1, wherein one or more means for attaching the primary wrap are operatively associated along the first and second peripheral edges of the primary wrap for securing the primary wrap around the leg.

4. A therapeutic compression apparatus as recited in claim 1, wherein the at least one inflatable bladder forms a predetermined gradient pressure profile when the at least one inflatable bladder is filled.

5. A therapeutic compression apparatus as recited in claim 1, further comprising at least one means for adjusting pressure coupled to the at least one inflatable bladder for controlling an amount of pressure supplied to the treatment site on the leg by the primary wrap.

6. A therapeutic compression apparatus as recited in claim 1, wherein the at least one inflatable bladder includes a plurality of fluid chambers.

7. A therapeutic compression apparatus as recited in claim 1, wherein the foot wrap is attached to the stirrup.

8. A therapeutic compression apparatus as recited in claim 1, wherein the foot wrap is configured as an adjustable strap to be positioned around the foot.

9. A therapeutic compression apparatus as recited in claim 1, further comprising an adjustable belt along a proximal horizontal edge of the primary wrap for securing the primary wrap around the leg.

10. A therapeutic compression apparatus as recited in claim 1, wherein the composite material is provided with a plurality of stitched darts and gathers for contouring the primary wrap to the leg.

11. A therapeutic compression apparatus as recited in claim 1, wherein the composite material is configured to remain stiff and prevent stretching of the primary wrap when the at feast one inflatable bladder is filled.

* * * * *